United States Patent [19]

Lau et al.

[11] Patent Number: 4,465,833

[45] Date of Patent: Aug. 14, 1984

[54] PROCESS FOR PREPARING ETHYNYLATED BENZOIC ACID DERIVATIVES

[75] Inventors: Kreisler S. Y. Lau, Alhambra; Robert H. Boschan, Los Angeles, both of Calif.

[73] Assignees: Hughes Aircraft Company, El Segundo, Calif.; Hughes Aircraft Company, El Segundo, Calif.

[21] Appl. No.: 197,300

[22] Filed: Oct. 15, 1980

[51] Int. Cl.$^3$ .................. C07D 239/70; C07D 307/89; C07D 233/54; C07D 213/06

[52] U.S. Cl. .................................. 544/246; 544/247; 568/426; 568/435; 568/463; 568/705; 548/335; 549/29; 549/506; 546/350; 260; 260/465 R; 560/100; 560/102; 560/104; 564/180; 564/183; 564/184; 564/161; 562/405

[58] Field of Search ................ 585/534; 568/426, 435, 568/436, 463, 465, 705, 807, 812, 424, 439; 562/405, 442, 443, 450, 453, 441, 433; 260/465 D, 346.11; 560/215, 100, 102, 104; 544/246, 247

[56] References Cited

U.S. PATENT DOCUMENTS

| | | | |
|---|---|---|---|
| 3,068,239 | 12/1962 | Miller | 560/104 |
| 3,533,774 | 10/1970 | Nau't | 71/1 |
| 3,852,364 | 12/1974 | Diamond | 560/102 |
| 3,987,116 | 10/1976 | Diamond | 560/100 |
| 4,101,591 | 7/1978 | Diamond | 568/424 |
| 4,105,786 | 8/1978 | Diamond | 568/424 |
| 4,125,563 | 11/1978 | Boschan | 568/424 |
| 4,139,561 | 2/1979 | Onopchenko | 564/423 |
| 4,204,078 | 5/1980 | Sabourin et al. | 568/705 |
| 4,210,610 | 7/1980 | Sabourin et al. | 568/807 |
| 4,223,172 | 9/1980 | Sabourin et al. | 568/812 |

OTHER PUBLICATIONS

Chemical Abstracts, 75, (13), p. 334, Abstract No. 88262u, (Sep. 27, 1971).
Journal of the American Chemical Society, 96, (7), 2010–2014, (Apr. 3, 1974).
Bulletin of the Academy of Sciences of the U.S.S.R., 28, (9, part 2), p. 1982, (Sep. 1979).
Journal of Organic Chemistry, 37, (20), 3185–3187, (Oct. 6, 1972).
Bulletin of the Chemical Society of Japan, 44, (8), 2237–2248, (Aug. 1971).
Chemical Abstracts, 89, (17), Abstract No. 146700n, p. 591, (Oct. 23, 1978).
Chemische Berichte, 100, (12), 3901–3915, (1967).
Journal of Organic Chemistry, 46, (11), 2280–2286, (May 22, 1981).
Journal of Organometallic Chemistry, 93, (2), 259–263, (1975).
Chemical Abstracts, vol. 82, #124330v, Gaetano, 1974.
Chemical Abstracts, vol. 82, #31037g, Kozorezov et al., 1974.
Takahashi, Synthesis, 1980, 627–630, "A Convenient Synthesis of Ethymylarenes and Diethynylarenes".

Primary Examiner—Natalie Trousof
Assistant Examiner—Raymond Covington
Attorney, Agent, or Firm—D. W. Collins; W. J. Bethurum; A. W. Karambelas

[57] ABSTRACT

A novel ethynylation process is disclosed which provides an expanded series of novel ethylnyl-terminated aromatic compounds having base sensitive substituents and which facilitates the economic preparation of prior art ethynyl-substituted aromatic compounds.

8 Claims, No Drawings

PROCESS FOR PREPARING ETHYNYLATED BENZOIC ACID DERIVATIVES

The Government has rights in this invention pursuant to Contract No. FF33615-78C-5197 awarded by the United States Airforce.

TECHNICAL FIELD

This invention relates generally to the preparation of ethynyl substituted aromatic compounds and, more particularly, to the preparation of substituted phenylacetylenes.

BACKGROUND OF THE INVENTION

1. Field of the Invention

This invention is embodied in a novel process for ethynylating aromatic compounds, which yields a series of novel ethynylated compounds and also provided a more efficient method for the production of certain prior art ethynylated compounds.

Compounds prepared by the process described and claimed below are suitable for use in the synthesis of various acetylene-terminated benzimidazoles and acetylene-terminated benzimidazoquinazolines that are useful as high temperature structural resins.

In addition to facilitating the preparation of novel acetylene-substituted aromatic compounds, the process of this invention provides an improved method for the synthesis of aminophenylacetylenes, hydroxyphenylacetylenes and halogenated phenylacetylenes which are important intermediates in acetylene-terminated polyimide and polyimide oligomers and polymers.

2. Description of the Prior Art

An example of prior art, known to applicants, and possibly relevant to this invention is described in an article entitled the "Synthesis of Ortho-Ethynylbenzaldehyde and an Approach to Dibenzoannulene" published by Juro Ojima, ET AL of Toyama University in Gufeku, Toyama, Japan in *Chemistry Letters* at pp. 633–636 in 1972. The process to prepare ortho-ethynylbenzaldehyde disclosed in the Toyama publication is a relatively inefficient multiple step process which provides relative low yields and is costly both in materials and in time consumed in preparing this compound.

A widely accepted procedure for the introduction of an acetylenic substituent onto an aromatic nucleus is known as the Stephens-Castro coupling reaction between an aryl iodide and a stoichiometric amount of a protected cuprous acetylide and pyridine at reflux. See C. E. Castro and R. D. Stephens, *J. Org. Chem.* 28, 2163 (1963). Commonly used protecting groups for acetylenes are acetals, ketones, ketals, hydroxymethyl and tetrahydrofuran-protected hydroxymethyl, dimethylcarbinol, ethyl vinyl ether-protected carbino, and ethyl ester. The removal of these groups often requires several steps and strongly alkaline media.

An elegant alternative to the above Stephens-Castro method rests in the coupling between arylcopper reagents and iodoethynyltrimethylsilane at below ambient temperatures. The removal of the trimethylsilyl group with weak alkaline is quantitative. However, the in situ preparation of the arylcopper reagents depends on prior formation of Grignard or lithium reagents, a requirement that forbids the presence of functional groups which are incompatible with the organometallic reagents.

One of the prior art methods most relevant to the present invention for preparing ethynalated compounds, and known to Applicants herein, is known as the Heck reaction, [R. F. Heck, *Accts of Chem. Res.*, Vol. 12, 146 (1979)] which is a reaction between phenylacetylene and aromatic halides in the presence of an organopalladium catalyst. A parallel procedure in effecting ethynylation of aromatic compounds employs the palladium catalyzed coupling of aromatic bromides and iodides with 2-methyl-3-butyn-2-ol. See C. A. Onopchenko, E. T. Sabourin, and C. M. Selwitz, *J. Org. Chem,* 44, 1233 (1979); E. T. Sabourin and C. M. Selwitz, U.S. Pat. No. 4,128,588. Dec. 5, 1978; A. Onopchenko, E. T. Sabourin, and C. M. Selwitz, U.S. Pat. No. 4,139,561. Feb. 13, 1979; E. T. Sabourin and C. M. Selwitz, U.S. Pat. No. 4,210,610. July 1, 1980; E. T. Sabourin and C. M. Selwitz, U.S. Pat. No. 4,223,172. Sept. 16, 1980; and also B. A. Reinhardt and F. E. Arnold, *United States Airforce Wright Aeronautical Laboratories Technical Report,* AFWAL-TR-80-4012, April, 1980. In all of the above publications, the removal of the acetonyl protecting groups requires sodium hydroxide in refluxing toluene. Therefore, base-sensitive groups cannot be present.

An entirely different process for the synthesis of aminophenylacetylenes is found in U.S. Pat. No. 3,928,450 issued to Norman Bilow on Dec. 23, 1975 and assigned to the present assignee. While the process disclosed in the above '450 Bilow patent is effective and serves its intended purpose, it also requires corrosive reactants and is difficult to operate, thereby resulting in an exceedingly expensive product.

SUMMARY OF THE INVENTION

The general purpose of this invention is to provide certain new and improved ethynylated aromatic compounds. In accomplishing this purpose while avoiding most, if not all, of the disadvantages of the prior art and at the same time retaining the advantages of said art, we have invented a new process for ethynylating aromatic compounds which increases the yields relative to certain processes for producing prior art ethynylated compounds, and this new process additionally provides an expanded series of new and useful ethynylated compounds.

Our process comprises the steps of (1) catalytically coupling a compound whose structure is:

where X may be I, Br, or Cl; G may be H, CHO, $-CO_2H$, $-CO_2G'$, $-CONH_2$, $-CONHG'$, or CN wherein G' may be an alkyl group having from 1 to 10 carbon atoms, an aryl group or a substituted aryl group; and where Ar may be an aromatic nucleus selected from the group comprising phenylenes, phenylene oxides, pyrenes naphthalene, anthracene, phenanthrene, aromatic imides, biphenyls, terphenyls, thiophenes, pyroles, furans, and pyridines, with a compound whose structure is Y—C≡CH, where Y is an end-protecting moiety selected from the group consisting of $-Si(CH_3)_3$, $-CHO$, and $-CH(OCH_3)_2$, by mixing said compounds at an elevated temperature in the presence of a mixture of a metal catalyst and a triarylphosphine ligand dissolved in a tertiary amine solvent to produce an end-protected ethynylated benzoic acid derivative and (2) subsequently removing said end-protecting moiety from said acid derivative by a potassium carbonate-catalyzed deprotection reaction, thereby yielding an ethynylated benzoic acid derivative that is suitable for use as an intermediate in the synsthesis ethynyl-terminated aromatic oligomers.

The novel compounds produced in accordance with our process include compounds whose structures are $HC\equiv C-Ar$ where AR equals benzaldehydes, benzoic acid esters, benzoic acids, benzamides, benzeneamines, aryl orthoesters, benzotrifluorides, benzonitriles, naphthalenes, pyrenes, anthracenes, phenanthrenes, phenylbenzimidazoles, phenylbenzimidazoquinazolines, aromatic imides, biphenyls, terphenyls, phenylene oxides, pyroles, thiophenes, furans, and pyridines.

It is therefore a purpose of this invention to provide a new class of ethynylated aromatic compounds.

An additional purpose of this invention is to provide a process for ethynylating aromatic compounds that does not require the use of corrosive starting material or reagents.

A still further purpose of this invention is to provide a process for preparing ethynylated aromatic compounds that is relatively inexpensive to operate and is suitable for scaling up to produce large quantities of said compounds.

That we have accomplished the above-stated purposes while avoiding the disadvantages of prior art and retaining most, if not all, of the advantages of the prior art, will be apparent upon reference to the following detailed description of the invention.

DETAILED DESCRIPTION OF THE INVENTION

This invention describes a novel and an efficient approach to the synthesis of a new class of ethynylated aromatic compounds under mild reaction conditions. Aromatic halides are coupled with acetylenic compounds, whose structures are $HC\equiv C-Y$ where Y is an end-protecting moiety selected from the group consisting of $-Si(CH_3)$, $-CHO$, and $-CH)(CH_3)_2$ to form end-protected arylacetylenes. The function of an end-protecting moiety, commonly known to the practitioners of chemical synthesis as a protecting group, is to protect a specific functional group from participating in a specified chemical transformation while another site on the same molecule can undergo the specified chemical reaction. After the specified chemical transformation is accomplished, the protecting group can be removed by a specific deprotection procedure regenerating the specific functional group.

This coupling reaction is accomplished by forming a solvent solution with the aromatic halide, the end-protected acetylene, a metal catalyst and a metal-stabilizing ligand and subsequently heating said solution to approximately 100° C. for a period of from 3 to 24 hours depending upon the reactivity of the aromatic halide.

Palladium acetate is a preferred metal catalyst. However, other metallic catalyst such as nickel acetate and platinum acetate may be employed. There are many ways to stabilize a metallic catalyst. We prefer to use ligands such as triarylphosphine, triarylstibine, and triarylarsine.

Any tertiary amine solvent may be used so long as the solvent is miscible with water. We prefer to use triethylamine as the solvent.

The halogen on the aromatic halide can be iodine, bromine, and sometimes chlorine. Our tests to date show bromine as a preferred halogen.

The aromatic nucleus can be a variety of compounds: for example, benzaldehydes, benzoic acid esters, benzoic acids, benzamides, benzonitriles, benzeneamines, aryl orthoesters, benzotrifluorides, anthracenes, phenanthrenes, naphthalenes, pyrenes, phenylbenzimidazoles, phenylbenzimidazoquinazolines, aromatic imines, biphenyls, terphenyls, pyroles, thiophenes, furans and phenylene oxides.

Mechanistically, two molecules of the acetylene undergo an oxidative addition-reductive elimination sequence with palladium[II] acetate to yield the Glaser product and a palladium[O] species. Oxidative addition of the aromatic halide, preferably bromide, to palladium is a facile process, generating arylpalladium[II] halide which is then captured by another acetylene molecule to yield an unstable palladium[IV] intermediate. Reductive elimination of the arylated acetylene and hydrogen bromide regenerates the palladium[O] species needed to maintain the catalytic cycle. The detailed mechanism of the oxidative addition steps between the aryl halide and palladium has been suggested as nucleophilic aromatic substitution, electrontransfer or "3-center" in nature. It is noteworthy that the nucleophilic nature of low-valent metals is emphasized in all three proposed mechanisms.

The process of this invention can be illustrated by the following reaction sequence:

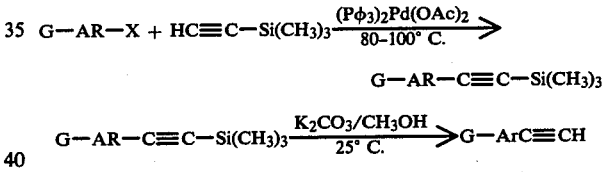

where G equals H, CHO, $CO_2G'$, $CO_2H$, $CONG_2'$, $NH_2$, $C(OG')_3$, $CF_3$ or CN, wherein G' may be an alkyl group having from 1 to 10 carbon atoms, an aryl group or a substituted aryl group, X may be a halogen such as chlorine, bromine or iodine and Ar is an aromatic or heteroaromatic nucleus selected from the group consisting of naphthalenes, pyrenes, anthracenes, phenanthrenes, phenylbenzimidazoles, phenylbenzimidazoquinazolines, aromatic imines, biphenyls, terphenyls, phenylene oxides, pyroles, thiophenes, furans, phenylenes and pyridines.

Example of the synthetic procedures are illustrated below.

EXAMPLE I p-Ethynylbenzaldehyde

To a deaerated solution of 25.0 g (130 mmoles) of p-bromobenzaldehyde, 1 g of triphenylphosphine in 25.0 ml of anhydrous triethylamine were added in succession 20.0 g (204 mmoles) of ethynyltrimethylsilane and 0.3 g of palladium acetate. The mixture was heated at reflux under argon for 5 hours and the white precipitate of triethylamine hydrobromide was filtered. (Near quantitative amount of the amine salt could be routinely isolated.) The filtrate was concentrated to a viscous oil which crystallized as long needles upon standing. Passing the product through silica gel and recrystallizing from hexane yielded 25.5 g (126 moles, 97%) of p-trimethylsilylethynylbenzaldehyde: mp 66°–67°; ir (KBr) 2960 (medium, sharp, SiC—H), 2825, 2720 (medium, sharp, HC=O), 2145 (medium, sharp C≡C), 1690 (v. strong, broad, C=O), 1245 (strong, sharp, SiC) and 840 cm$^{-1}$ (strong, broad, Si—C); mass spectrum: m/e 202 (15.8%, M+), 187 (100%, M—CH$_3$); nmr (CDCl$_3$): δ0.21 (s, 9H, Si—CH$_3$), 7.60 (q, 4H, J=7.0 Hz, aromatic), and 9.85 ppm (s, 1H, CHO).

Anal. Calc. for C$_{12}$H$_{14}$OSi: C, 71.23; H, 7.33; Si, 13.88. Found: C, 71.31; H, 7.42; Si, 14.01.

A solution of 16.0 g (79.2 mmoles) of p-trimethylsilylethynylbenzaldehyde in 50 ml of methanol was treated with 1 gm of potassium carbonate and the mixture was stirred under argon at 25° C. for two hours. The solvent methanol was removed and 100 ml of methylene chloride was added. The mixture was washed with aqueous sodium bicarbonate solution. The organic phase was separated, dried over magnesium sulfate and concentrated to a solid mass. The crude yield of p-ethynylbenzaldehyde was 10.3 g (79.2 moles, 100%). Further purification was carried out by sublimation at 80°–90° C./0.025–0.25 mm Hg to give white crystals: mp 88°–90°; ir (KBr) 3240 (medium, sharp, C≡CO), 2860, 2740 (weak, sharp, O=CH), 2100 (weak, sharp, C≡C), 1690 (strong broad, C=O) and 1590 cm$^{-1}$ (medium, sharp C=C); mass spectrum: m/e 130 (100%, M.+), 129 (90.7%, M.+ —H), 101 (59.0% M.+ —CHO); nmr (CDCl$_3$): δ3.21 (s, 1H, C≡C—H), 7.62 (distorted q, 4H, aromatic) and 9.88 ppm (s, 1H, CHO).

Anal. Calc. for C$_9$H$_6$O: C, 83.06; H, 4.65. Found: C, 82.90; H, 4.66.

EXAMPLE 2

6-(m-Ethynylphenyl)benzimidazoquinazoline

A slurry of 3.00 g (9.02 mmoles) of 6-bromophenyl)benzimidazoquinazoline, 100 mg of diacetatobis(triphenylphosphine)palladium[II] in 150 ml of 2:1 triethylamine-toluene was heated to 100° C. under argon and then treated with dropwise addition of 1.57 g (16.0 mmoles) of ethynyltrimethylsilane. After 3.5 hours, the mixture was cooled and filtered. The filtrate was diluted with 100 ml of ether, washed with 200 ml each of 5% hydrochloric acid and water, and then dried over magnesium sulfate. Concentrating the clear solution yielded a solid mass which upon trituration with hexane gave 2.21 g (56.5 mmoles, 70.5%) of 6-(m-trimethylsilylethynylphenyl)benzimidazoquinazoline: ir (KBr): 3077 (medium, sharp, C-H), 2960 (medium, sharp, SiCH), 2155 (strong, sharp, C≡C), 1621, 1587 (v. strong, sharp, C=N), 1524, 1456, 1441, 1355, 1325 (strong, sharp, C=C), 1247 (v. strong, sharp, Si—C) and 844 cm$^{-1}$ (v. strong, broad, Si—C bending); mass spectrum (70 ev) m/e 391.

A slurry of 2.00 g (5.12 mmoles) of 6-(m-trimethylsilylethynylphenyl)benzimidazoquinazoline and 200 mg of anhydrous potassium carbonate in 100 ml of anhydrous methanol was stirred at 25° for 3 hours. The solvent was removed and the residue was dissolved in 100 ml of chloroform, washed with 100 ml of 5% hydrochloric acid and then with 100 ml of water. The organic phase was dried over magnesium sulfate and concentrated to give a yellow solid which was recrystallized from ether-hexane. Yield: 1.55 g (4.86 mmoles, 94.9%): ir (KBr) 3300 cm$^{-1}$ (medium, sharp, C≡C—H); mass spectrum (70 ev) m/e 319 (molecular ion).

EXAMPLE 3

10-Ethynyl-6-(3'-ethynylphenyl)benzimidazoquinazoline

A slurry of 1.0 g (22.1 mmoles) of 10-bromo-6-(3'-bromophenyl)benzimidazoquinazoline in 400 ml of a 1:1 triethylamine-toluene mixture was deaerated and heated to 100° under argon. The solids did not dissolve completely. The catalyst (500 mg of triphenylphosphine and 250 mg of palladium[II] acetate) was introduced and the entire mixture was treated with dropwise addition of 10.0 g (102 mmoles) of ethynyltrimethylsilane.

After 30 minutes, more solids appeared to be dissolved, and the supernatent solution acquired an orange tint. As the reaction progressed, the solution slowly turned greenish-brown and the precipitate that was visible has a different texture from that of the initial slurry.

After 4 hours, thin-layer chromatography (silica gel) of the reaction mixture revealed the absence of starting material and the presence of a highly fluorescent material as product. The reaction mixture was cooled and filtered to yield 7.890 g (42.9 mmoles, 97.0%) of triethylamine hydrobromide. The filtrate was concentrated and the solid residue dissolved in 100 ml of ether, washed in succession with 100 ml of 10% hydrochloric acid, 100 ml of saturated sodium bicarbonate and 100 ml of water. After drying over magnesium sulfate, the ethereal solution was concentrated to yield a pale yellow solid mass which was washed with 100 ml of hexane and air-dried. The yield was 8.20 g (16.8 moles, 76.2%); mp 245°–246.5°; ir (KBr) 2959 (strong, sharp, SiC—H), 2155 (strong, sharp, —C≡C—), 1618, 1587 (strong, sharp, C=N), 1497, 1473, 1408, 1355 (all strong and sharp, C=C), 1247 cm$^{-1}$ (v. strong, sharp, Si—C); mass spectrum m/e 489 (100%, M.+ 2H), 473 (51.4%, M.+ +2H—CH$_3$); nmr (CDCl$_3$) δ0.27, 0.48 (2s, 18H, SiCH$_3$), and 7.30–8.00 ppm (m, 12H, aromatic).

A slurry of 7.50 g (15.4 mmoles) of 10-trimethylsilylethynyl-6-(3'-trimethylsilylethynylphenyl)benzimidazoquinazoline and 1.0 g of anhydrous potassium carbonate in 150 ml of a 2:1 methanol-toluene mixture was stirred under argon at 25°. After 15 minutes, the solids dissolved to yield a dark brown solution. Complete disappearance of the starting material was effected in 45 minutes, as revealed by thin-layer chromatography. The solvents were removed and the yellow residue was dissolved in 200 ml of dichloromethane, washed with 200 ml of 5% hydrochloric acid, and dried over magnesium sulfate.

Removal of solvent gave a pale yellow powdery solid: yield, 5.30 g (15.4 mmoles, 100%); mp>220°; ir (KBr) 3300 (strong, sharp, C≡C—H), 2110 (weak, sharp, C≡C), 2110 (weak, sharp, C≡C), 1625, 1590 (strong, sharp, C=N), 1530, 1480, 1450, 1360, 1330 cm$^{-1}$ (strong, sharp); mass spectrum: m/e 343 (100%, M.+) and no other significant peaks; nmr (CDCl$_3$) δ3.17, 3.27 (2s, 2H, C≡C—H) and 7.30–8.10 ppm (m, 12H, aromatic). An analytical sample was prepared by column chromatography (silica gel, 1:1 dichloromethane-hexane).

Anal. Calc. for C$_{24}$H$_{13}$N$_3$.1.5H$_2$O(370.4): C, 77.82; H, 4.35; N, 11.34. Found: C, 77.56; H, 3.92; N, 11.02.

EXAMPLE 4

Meta-ethynylbenzaldehyde

This example is similar to Example 1 except that m-bromobenzaldehyde was used instead of p-bromobenzaldehyde. The yield of m-trimethylsilylethynylbenzaldehyde was 80.2%: bp 120°–122° C./0.15 mmHg; ir (KBr) 2958 (medium, sharp, SiCH$_3$), 2825, 2717 (medium, sharp, CHO), 2146 (medium, sharp, C≡C), 1692 (strong, broad, C=O), 1244 (strong, sharp, Si—C) and 843 cm$^{-1}$ (strong, broad, Si—C); mass spectrum m/e 202 (16.4%, M.+), 187 (100%, M.+ CH$_3$); nmr (CDCl$_3$) δ0.22 (s, 9H, SiCH$_3$), 7.15 7.93 (m, 4H, aromatic) and 9.85 ppm (s, 1H, CHO).

Anal. Calc. for C$_{12}$H$_{14}$O Si: C, 71.23; H, 6.97; Si, 13.88 Found: C, 71.10 H, 7.07 Si, 14.04.

The yield of m-ethynylbenzaldehyde was 83.7%: mp 76°–76.5° C.; ir (KBr) 3240 (medium, sharp, C≡CH), 2860, 2740 (weak, sharp, O=C—H), 2100 (weak, sharp, C≡C), 1686 (strong, broad, C=O), and 1587 cm$^{-1}$ (medium, sharp, C=C); mass spectrum m/e 130 (100%, M.+), 129 (90.7%, M.+—H), 102 (18.6%), 101 (60.7%, M.+ CHO); nmr (CDCl$_3$) δ3.12 (s, 1H, C≡C—H), 7.16 8.00 (m, 4H, aromatic), and 9.85 ppm (s, 1H, CHO).

Anal. Calc. for C$_9$H$_6$O: C, 83.06; H, 4165. Found: C, 83.06; H, 4.78.

EXAMPLE 5

Methyl meta-Ethynylbenzoate

This example is similar to Example 1 except that methyl m-bromobenzoate was used instead of p-bromobenzaldehyde.

The yield of methyl m-(trimethylsilyl)ethynylbenzoate was 70%; bp 79°–85° C./0.001 mmHg; ir (film) 2970 (medium, sharp, SiCH$_3$), 2170 (medium, sharp, C≡C), 1735 (strong, sharp, C=O), 1295 (strong, broad, —O—), 1250, cm$^{-1}$ (strong, v. sharp, Si—C); mass spectrum m/e 232 (molecular ion).

The yield of methyl m-ethynylbenzoate was 79.8%; mp 48°–50° C.; ir (film) 3305 (strong, broad, C=O), 1300 cm$^{-1}$ (v. strong, broad, —O—); mass spectrum m/e 160 (molecular ion); nmr (CDCl$_3$) δ3.10 (S, 1H, C≡C—H), 3.91 (s, 3H, C)$_2$CH$_3$), and 7.33–8.17 ppm (m, 4H, aromatic).

Anal. Calc. for C$_{10}$H$_8$O$_2$: C, 74.99; H, 5.03. Found: C, 74.77; H, 5.34.

EXAMPLE 6

Methyl para-Ethynylbenzoate

This example is similar to Example 1 except that methyl p-bromobenzoate was used instead of p-bromobenzaldehyde.

The yield of methyl p-(trimethylsilyl)ethynylbenzoate was 69.0%; mp 55.0°–55.5°; ir (KBr) 2960 (medium, sharp, SiCH$_3$), 2160 (medium, sharp, C≡C), 1718 (strong, sharp, C=O), 1597 (medium, sharp, C=C), 1274 (strong, broad, —O—), 1242 cm$^{-1}$ (strong, sharp, Si—C); mass spectrum m/e 232 (molecular ion).

The yield of methyl para-ethynylbenzoate was 73.1%; mp 9.25°–93.5° C.; ir (KRB) 3226 (strong, sharp, C≡CH), 2092 (weak, sharp, C≡C), 1695 (v. strong, v. broad, C=O) and 1274 cm$^{-1}$ (v. strong, v. broad, ester —O—); mass spectrum (70 ev) m/e 160 (mt); nmr (CPCl$_3$) δ3.19 (s, 1H, C≡CH), 3.88 (s, 3H, CO$_2$CH$_3$), and 7.70 ppm (q, 4H, JAB=8.0 Hz, aromatic).

Anal. Calc. for C$_{10}$H$_8$O$_2$: C,74.99; H, 5.03. Found: C,75.11; H, 5.16.

INDUSTRIAL APPLICABILITY

The process disclosed above facilitates the preparation of an expanded series of commercially useful ethynylated aromatic compounds having base sensitive substituents. While it is recognized that certain selected compounds belonging to the class of compounds prepared in accordance with our process are known, these prior art ethynylated compounds had limited commercial value because of the expense associated with their production by conventional ethynylation processes.

Compounds prepared in accordance with this invention will have their greatest utility as intermediates in the synthesis of ethynyl-terminated polyimide oligomers. These oligomers have been demonstrated to be exceedingly useful in the preparation of high strength, high temperature stability composites.

Having completely disclosed our invention and provided teachings which, if followed, will enable others to make and use the same, the scope of our claims may now be understood as follows:

What is claimed is:

1. A process for preparing ethynylated benzoic acid derivatives in high yield that comprises the steps of:

A. catalytically coupling a compound whose structure is

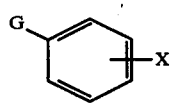

where G may be H, CHO, —CO$_2$G', —CONH$_2$, CONHG' or CN wherein G' may be an alkyl group having from 1 to 10 carbon atoms, an aryl group or a substituted aryl group, and X may be I, Cl, or Br with a compound whose structure is

where Y is an end-protecting moiety selected from the group consisting of —Si(CH$_3$)$_3$, —CHO, and —CH(OCH$_3$)$_2$, by heating a solution of said compounds in the presence of a metal catalyst thereby producing an end-protected ethynylated benzoic acid derivative; and B. subsequently, removing said end-protective moiety from said acid derivative by a base-catalyzed deprotective reaction, thereby yielding an ethynylated benzoic acid derivative that is suitable for use as an intermediate in the synthesis of ethynyl-terminated aromatic oligomer.

2. The process of claim 1 wherein said metal catalyst is selected from the group consisting of palladium acetate, platinum acetate and nickel acetate.

3. The process of claim 1 wherein said heated solution is comprised of a palladium acetate catalyst stabilized with triarylphosphine.

4. A process for introducing an acetylenic substituent onto an aromatic nucleus in high yields without damaging previously appendaged base-sensitive groups comprising the steps of:

A. catalytically coupling a first compound, whose structure is

where G is a moiety selected from the group consisting of H, CHO, $CO_2H$, $CO_2G'$, $CONHG'$, $CONH_2$ and CN wherein G' may be an alkyl group having from 1 to 10 carbon atoms, an aryl group, or a substituted aryl group, X is a halogen selected from the group consisting of I, Cl, and Br, and Ar is an aromatic or hetero-aromatic nucleus selected from the group consisting of phenylene, aromatic imides, biphenyls, terphenyls, phenylene oxides, pyrenes, naphthalenes, thiophenes, furans, and pyridines, with a second compound whose structure is

Y—C≡CH where Y is an end-protecting moiety selected from the group consisting of —$Si(CH_3)_3$, —CHO, and $CH(OCHH_3)_2$, by mixing said compounds at an elevated temperature in the presence of a catalyst dissolved in a tertiary amine solvent thereby producing an end-protected ethynyl-substituted aromatic nucleus; and B. subsequently removing said end-protecting moiety from said nucleus by exposing said moiety to a base-catalyzed deprotective reaction thereby yielding an ethynylated aromatic compound that is suitable for use in the synthesis of ethynyl-terminated aromatic oligomers.

5. The process of claim 3 wherein said aromatic nucleus is a benzoic acid derivative and said process yields ethynylated benzoic acid derivatives.

6. The process of claim 3 wherein said aromatic nucleus is either meta benzaldehyde or para benzaldehyde and said end-protecting moiety is $Si(CH_3)_3$.

7. A process of claim 3 wherein the structure of said first compound is

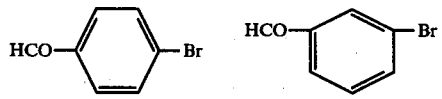

said second compound is HC≡C—$Si(CH_3)_3$, a palladium catalyst is employed and a mixture of methanol and potassium carbonate is used to remove said end-protecting group.

8. A process for ethynylating an aromatic nucleus having a base-sensitive substituent thereon without damaging said substituent comprising the steps of:
(a) catalytically coupling an aromatic halide having a base-sensitive substituent thereon with a mono-substituted acetylene, in the presence of a metal catalyst, thereby forming an end-protected arylacetylene; and
(b) subsequently regenerating said base-sensitive substituent by exposing said end-protected arylacetylene to a deprotective reaction.

* * * * *